United States Patent
Masubuchi (10) Patent No.: US 10,285,718 B2
(45) Date of Patent: May 14, 2019

(54) CATHETER SYSTEM (71) Applicant: TERUMO KABUSHIKI KAISHA, Shibuya-ku, Tokyo (JP)

(72) Inventor: Yuuki Masubuchi, Hiratsuka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 112 days.

(21) Appl. No.: 15/067,360

(22) Filed: Mar. 11, 2016

(65) Prior Publication Data
US 2016/0270803 A1    Sep. 22, 2016

(30) Foreign Application Priority Data

Mar. 20, 2015 (JP) ................................ 2015-058311

(51) Int. Cl.
*A61B 17/22* (2006.01)
*A61B 17/3207* (2006.01)
*A61B 17/00* (2006.01)

(52) U.S. Cl.
CPC .......... *A61B 17/22* (2013.01); *A61B 17/3207* (2013.01); *A61B 17/320783* (2013.01);
(Continued)

(58) Field of Classification Search
CPC ............. A61B 17/22; A61B 2217/005; A61B 2017/22067; A61B 2017/00398;
(Continued)

(56) References Cited

U.S. PATENT DOCUMENTS

| | | | | |
|---|---|---|---|---|
| 5,599,304 A | * | 2/1997 | Shaari | A61M 1/008 604/173 |
| 2004/0111069 A1 | * | 6/2004 | Schaaf | A61M 16/0463 604/284 |

(Continued)

FOREIGN PATENT DOCUMENTS

| | | |
|---|---|---|
| JP | 2009-504343 A | 2/2009 |
| JP | 2013-126573 | 6/2013 |

(Continued)

OTHER PUBLICATIONS

Office Action (Notification of Reasons for Refusal) dated Oct. 29, 2018, by the Japanese Patent Office in corresponding Japanese Patent Application No. 2015-058311 and an English Translation of the Office Action. (7 pages).

*Primary Examiner* — Richard G Louis
(74) *Attorney, Agent, or Firm* — Buchanan Ingersoll & Rooney PC (57) ABSTRACT

A catheter system includes a shaft main body having a rotation axis lumen including a rotation central axis, a revolving lumen that revolves around the rotation axis lumen when the shaft main body is rotated about the rotation central axis, a side-by-side portion in which at least a portion of the rotation axis lumen and at least a portion of revolving lumen exist in side-by-side relationship, and a branch part at which the revolving lumen branches off from the side-by-side portion on a distal side relative to the branch part. The revolving lumen on the distal side relative to the branch part is formed of a distal shaft which has a proximal-side bending portion that bends in such a direction as to become farther away from the rotation axis lumen in radial direction and an opening that communicates with the revolving lumen.

12 Claims, 6 Drawing Sheets

(52) U.S. Cl.
CPC .......... *A61B 2017/00398* (2013.01); *A61B 2017/22067* (2013.01); *A61B 2017/22079* (2013.01); *A61B 2217/005* (2013.01)

(58) Field of Classification Search
CPC ........ A61B 17/3207; A61B 17/320783; A61B 2017/22079
See application file for complete search history.

(56) References Cited

U.S. PATENT DOCUMENTS

| | | | |
|---|---|---|---|
| 2004/0181188 A1* | 9/2004 | Schaer | A61B 18/1492 604/95.04 |
| 2006/0063973 A1* | 3/2006 | Makower | A61B 1/00135 600/114 |
| 2007/0225661 A1* | 9/2007 | Ash | A61M 25/0021 604/284 |
| 2008/0208230 A1* | 8/2008 | Chin | A61B 17/1617 606/167 |

FOREIGN PATENT DOCUMENTS

| | | |
|---|---|---|
| WO | 01/45572 A1 | 6/2001 |
| WO | 2007/022383 A2 | 2/2007 |

\* cited by examiner

CATHETER SYSTEM

CROSS-REFERENCES TO RELATED APPLICATIONS

This application claims priority to Japanese Application No. 2015-058311 filed on Mar. 20, 2015, the entire content of which is incorporated herein by reference.

TECHNICAL FIELD

The present disclosure relates to a catheter system, and in particular to catheter system configured to remove, by suction, a thrombus which has been generated in a living body lumen.

BACKGROUND DISCUSSION

When a thrombus is discovered to have been generated in a living body lumen, it can be necessary to rapidly remove the thrombus. For example, rapid removal is generally called for upon discovery of deep venous thrombosis, in which a thrombus has been generated in a femoral, popliteal, or other deep-region vein.

In one method of treatment for deep venous thrombosis, a catheter is inserted into a blood vessel and a medication, such as a thrombolytic agent, is injected to an embolized region to dissolve the thrombus. However, such a method can lead to undesired side effects such as bleeding.

A method of treatment in which a thrombus is removed by suction via a catheter inserted into a blood vessel has also been proposed. Such a method can avoid the use of a medication or minimize the dosage to a small amount. An example of a catheter which can be used in such a treatment is disclosed in Japanese Patent Laid-Open No. 2013-126573.

SUMMARY

When sucking a thrombus by a catheter, a suction force is generated in an effective range of up to about 2 to 3 mm from the suction port of the catheter. Therefore, in a case in which the diameter of the blood vessel is relatively large, it can become necessary to carry out rotation of the catheter in the blood vessel in order to suck a thrombus up which is located outside the effective suction range of the suction port of the catheter. However, it can be difficult to perform the suction thoroughly across the whole section orthogonal to the axial direction in the blood vessel.

The present disclosure is made in view of these and other issues to provide a catheter system by which suction can be easily performed thoroughly across the whole section orthogonal to the axial direction in a blood vessel. A catheter system according to the present disclosure has a shaft main body having an elongated shape. The shaft main body has a rotation axis lumen including a rotation central axis and a revolving lumen that revolves around the rotation axis lumen when the shaft main body is rotated about the rotation central axis. The shaft main body includes a branch part at which the revolving lumen branches off from the side-by-side portion on a distal side relative to the branch part, and the revolving lumen on the distal side relative to the branch part is formed of a distal shaft. The distal shaft has a proximal-side bending portion that bends in such a direction as to become farther away from the rotation axis lumen in the radial direction and an opening that communicates with the revolving lumen.

In the catheter system configured as above, in association with the rotation of the rotation axis lumen, the revolving lumen revolves around the rotation axis lumen and the distal shaft having the bending portion undergoes rotation with a relatively large radius of curvature in the section orthogonal to the axial direction of a blood vessel. Thus, the catheter system can effectively suck and remove the thrombus in blood vessels having a wide range of sizes.

BRIEF DESCRIPTION OF THE DRAWINGS

FIGS. 11A and 11B are front views of a part around a distal shaft of a fourth modification example; FIG. 11A illustrates the case in which the distal shaft is present at the central position of the outermost sheath body in the radial direction, and FIG. 11B illustrates the case in which the distal shaft is present at the peripheral part of the outermost sheath body in the radial direction;

DETAILED DESCRIPTION

An embodiment of the present disclosure will be described below with reference to the drawings. A catheter system 10 of the present embodiment is inserted into a blood vessel as a living body lumen and is used for a treatment of removing a thrombus in deep venous thrombosis. Note that the dimensional ratio of the drawing is exaggerated and is different from the actual ratio in some cases for convenience of explanation. Note also that, in the present specification, the side inserted into a blood vessel in a shaft main body 11 included in the catheter system 10 will be referred to as the "distal end" or "distal side," and the at-hand side that is operated will be referred to as the "proximal end" or "proximal side."

Figure 1:
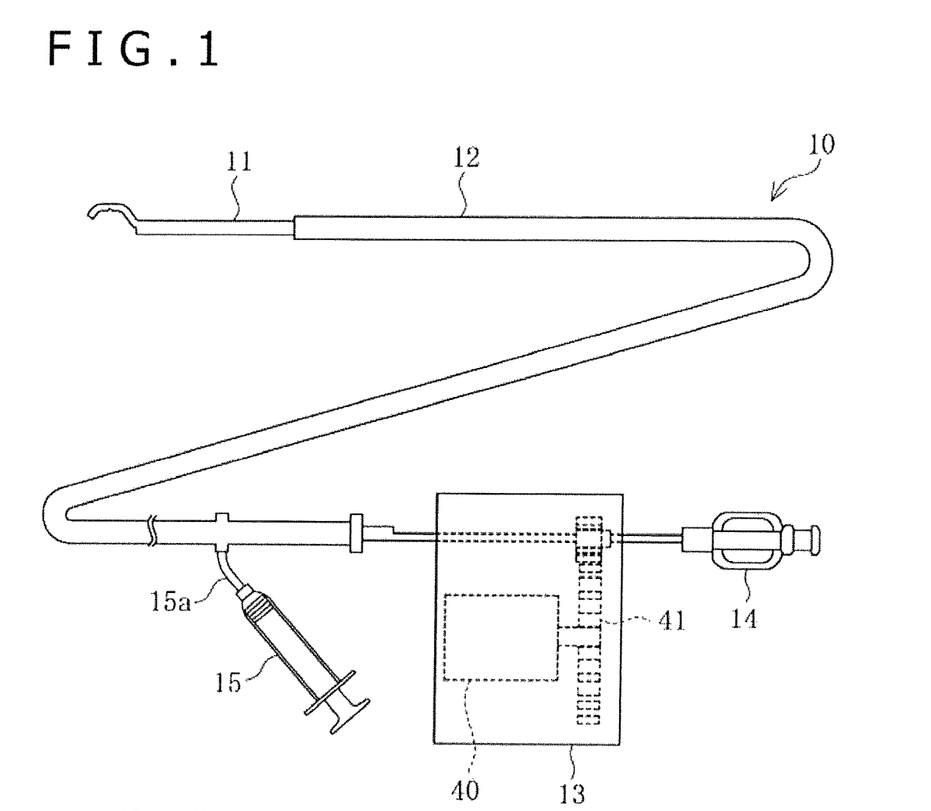
FIG. 1 is a front view representing the overall structure of a catheter system.

The catheter system 10 has the shaft main body 11 formed into an elongated shape, an outermost sheath body 12 that houses the shaft main body 11 and is slidable in the axial direction relative to the shaft main body 11, a rotational drive unit 13 that can rotate the shaft main body 11, a hub 14 provided at the proximal end portion of the shaft main body 11, and a syringe 15 connected to an intermediate position of the shaft main body 11. The syringe 15 can suck a hollow inside part of the shaft main body 11 and set the hollow inside part to a negative pressure state. This configuration can suck a thrombus from the distal portion of the shaft main body 11 inserted into a blood vessel.

The shaft main body 11 is formed by a material that is soft and has such a characteristic as to be capable of transmitting the power of rotation acting from the proximal side to the distal side. For example, a tubular body having a multilayer coil shape, such as a three-layer coil whose winding direction is set to the right, left, and right directions alternately, or a component obtained by burying a reinforcing member such as a wire rod into polyolefin such as polyethylene or polypropylene, polyamide, polyester such as polyethylene terephthalate, fluorine-based polymer such as ethylene tetrafluoroethylene (ETFE), polyether ether ketone (PEEK), polyimide, or a combination of them is used.

The constituent material of the outermost sheath body 12 is formed by, but not particularly limited to, a material having favorable slidability and mechanical strength. For example, polyolefin such as polyethylene or polypropylene, polyamide, polyester such as polyethylene terephthalate, fluorine-based polymer such as ETFE, PEEK, or polyimide can be favorably used. Furthermore, the outermost sheath body 12 may be formed by plural materials and a reinforcing member, such as a wire rod, may be embedded.

The rotational drive unit 13 has a drive motor 40 and a gear unit 41 that links the drive motor 40 with the shaft main body 11. Rotating the drive motor 40 can rotate the shaft main body 11 in the circumferential direction.

Figure 2:
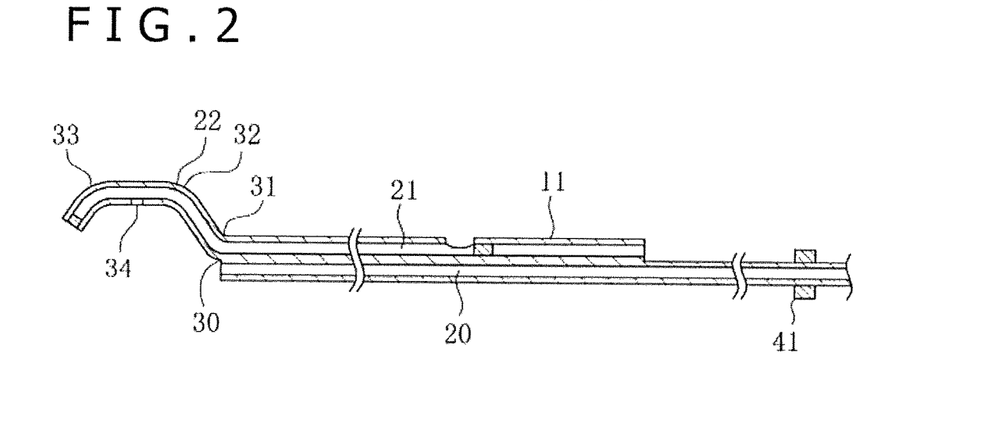
FIG. 2 is a sectional view of a shaft main body.

As shown in FIG. 2, the shaft main body 11 is formed to define two axially-extending spaces which extend together along the entire axial direction except for at the proximal end portion and at the distal end portion. In the shaft main body 11, one space is a rotation axis lumen 20 serving as the center of rotation by the rotational drive unit 13 and the other space is a revolving lumen 21 that revolves around the rotation axis lumen 20 in association with the rotation of the rotation axis lumen 20. In the present embodiment, into the rotation axis lumen 20, a shaft 60 of a balloon catheter having a balloon 61 is inserted such that the balloon 61 acts as a protective member disposed on the distal side relative to the distal portion of the shaft main body 11. Furthermore, into the shaft 60 of the balloon catheter, a guide wire (not shown) for guiding the shaft 60 of the balloon catheter and the shaft main body 11 in a blood vessel is inserted. The revolving lumen 21 is set to a negative pressure state by the syringe 15 and is used for suction of a thrombus sucked from an opening 34 made at the distal portion. Note that the protective member is not limited to the balloon 61 and may be a filter.

The rotation axis lumen 20 and the revolving lumen 21 are juxtaposed along the axial direction of the shaft main body 11 but branch apart at a branch part 30 near the distal end. The distal end of the rotation axis lumen 20 is present at the position of the branch part 30, and the revolving lumen 21, on the distal side relative to the branch part 30, is formed of a distal shaft 22.

The distal shaft 22 has the following portions on the distal side relative to the branch part 30: a proximal-side bending portion 31 that bends in such a direction as to become farther away from the rotation axis lumen 20 in the radial direction; a first distal-side bending portion 32 that bends on the distal side relative to the proximal-side bending portion 31; and a second distal-side bending portion 33 that bends on the distal side relative to the first distal-side bending portion 32. Furthermore, the opening 34 that communicates with the revolving lumen 21 is formed between the first distal-side bending portion 32 and the second distal-side bending portion 33. Note that the opening may instead be formed in the distalmost surface of the distal shaft 22.

The revolving lumen 21 has a suction port 50 that communicates with the syringe 15 on the proximal side. The revolving lumen 21 on the proximal side relative to the suction port 50 is occluded, for example, by a sealing member sealingly fitted in the revolving lumen 21 on the proximal side relative to the suction port 50. Furthermore, the rotation axis lumen 20 extends to the proximal side relative to the proximal end portion of the revolving lumen 21. Part of the gear unit 41 linked with the drive motor 40 is provided at the proximal portion of the shaft main body 11. This enables rotational driving around the rotation axis lumen 20. Note that the central axis of the rotation axis lumen 20 serves as the rotation central axis in the present embodiment. However, it suffices that the rotation axis lumen 20 includes the rotation central axis.

Figure 3:
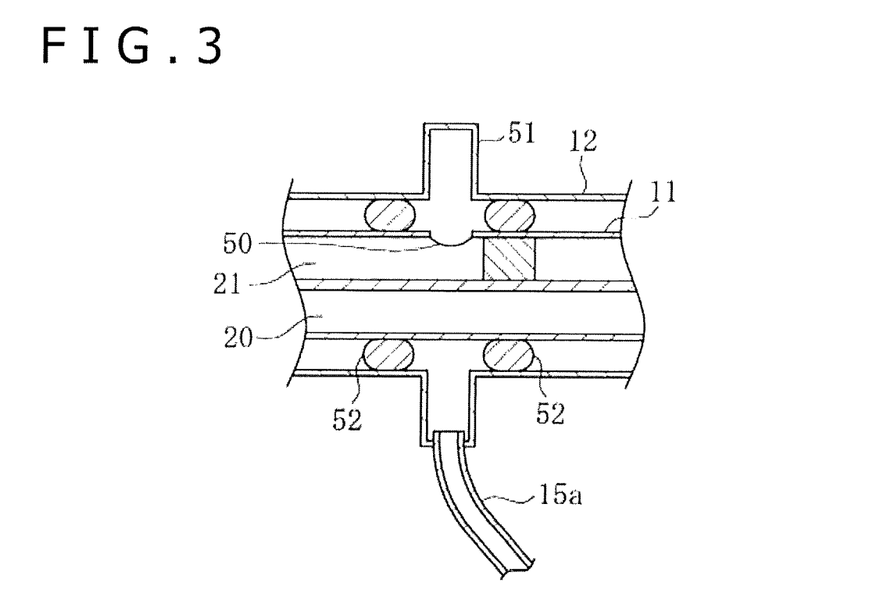
FIG. 3 is an enlarged sectional view of a connecting part between the shaft main body that rotates and a syringe.

The structure for suction of a hollow inside part of the shaft main body 11 that rotates will be described. As shown in FIG. 3, a hollow circumferential protruding portion 51 is formed in the outermost sheath body 12. A connecting tube 15a that communicates with the syringe 15 is attached to this circumferential protruding portion 51, so that the connecting tube 15a communicates with the hollow inside part of the outermost sheath body 12.

Between the shaft main body 11 and the outermost sheath body 12, an O-ring 52 is provided on each of the distal side and proximal side of the suction port 50 of the shaft main body 11, with the suction port 50 interposed between the O-rings 52. The O-rings 52 can block the flow of a fluid in the axial direction within the space between the shaft main body 11 and the outermost sheath body 12 and allow the shaft main body 11 to rotate relative to the outermost sheath body 12. That is, the part communicating with the suction port 50 in the space between the shaft main body 11 and the outermost sheath body 12 is in the state of being hermetically sealed from the other part by the O-rings 52.

Due to this, the revolving lumen 21 communicates with the syringe 15, which can set the inside of the revolving lumen 21 to a negative pressure state by pulling back the plunger of the syringe 15 and suck a thrombus and so forth into the opening 34 at the distal portion. Furthermore, because the shaft main body 11 can rotate relative to the outermost sheath body 12, it is also possible to perform suction from the revolving lumen 21 simultaneously with rotating the shaft main body 11.

Figure 4:
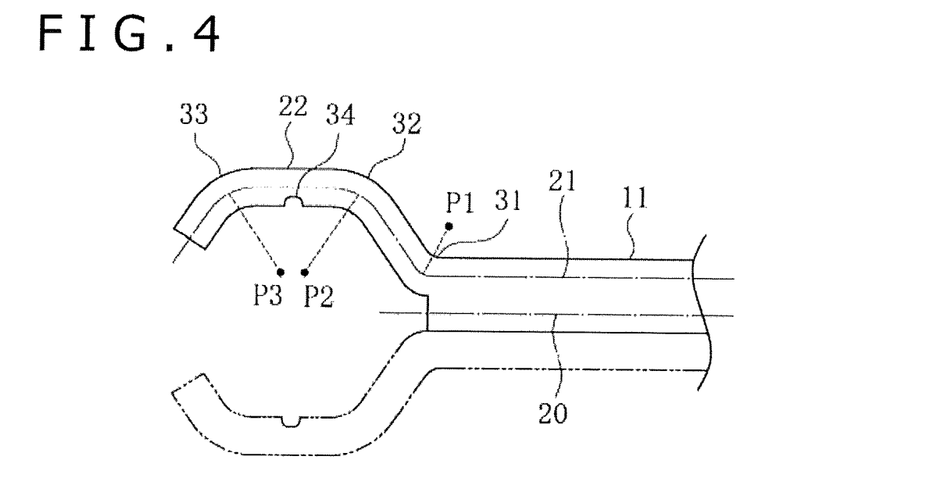
FIG. 4 is a front view of a part around the distal portion of the shaft main body.

When the rotation axis lumen 20 is rotated by the rotational drive unit 13, the revolving lumen 21 revolves around the rotation axis lumen 20 as shown in FIG. 4. Note that, in FIG. 4, the shaft main body 11 in the state resulting from rotation by 180 degrees is shown by an imaginary line in contrast to the shaft main body 11, which is drawn by a solid line. Regarding the distal shaft 22 forming the distal portion of the revolving lumen 21, a central point P1 that defines the radius of curvature in the central axis of the proximal-side bending portion 31 is located on the opposite side to the central axis of the rotation axis lumen 20. That is, the proximal-side bending portion 31 bends toward the outside of the shaft main body 11.

A central point P2 that defines the radius of curvature in the central axis of the first distal-side bending portion 32 is located on the side of the central axis of the rotation axis lumen 20. That is, the first distal-side bending portion 32 bends in such a direction at least so as not to extend toward the outside of the shaft main body 11. Moreover, a central point P3 that defines the radius of curvature in the central axis of the second distal-side bending portion 33 is also located on the side of the central axis of the rotation axis lumen 20, and the second distal-side bending portion 33 bends in such a direction as to extend toward the inside of the shaft main body 11.

As above, the first distal-side bending portion 32 and the second distal-side bending portion 33 of the distal shaft 22 bend in such a direction as not to extend to the outside of the shaft main body 11. Due to this, when the distal shaft 22 is located in a blood vessel and the shaft main body 11 rotates, the distalmost surface of the distal shaft 22, which can be relatively sharp compared to the side of the distal shaft 22, does not directly contact with the blood vessel wall, and damage to the blood vessel wall can be minimized.

Furthermore, the opening 34 of the distal shaft 22 is disposed to face the inside in the radial direction of rotation across the whole circumference when the distal shaft 22 rotates around the rotation central axis of the rotation axis lumen 20. The wall thickness of the distal shaft 22 can be relatively small and therefore the edge part of the opening 34 can be relatively sharp, and so the opening 34 could damage the blood vessel wall. However, in the present embodiment, because the opening 34 is disposed to face the inside in the radial direction across the whole circumference of rotation, the opening 34 can be prevented from directly contacting with the blood vessel wall, and damage to the blood vessel wall can be minimized.

Next, a method for using the catheter system 10 of the present embodiment will be described by taking the case of suction of a thrombus in a blood vessel as an example. At the stage before insertion of the shaft main body 11 of the catheter system 10 into the blood vessel, the distal portion of the shaft main body 11 including the distal shaft 22 is in the state of being housed in the outermost sheath body 12 as described above.

Before insertion of the shaft main body 11 into a blood vessel 80, a guide wire (not shown) is inserted into the blood vessel 80. Along this guide wire, first the shaft 60 of a balloon catheter is inserted into the blood vessel 80. The shaft 60 of the balloon catheter is inserted to the distal side relative to the thrombus and the balloon 61 is inflated by injection of an inflation fluid or the like. Due to the inflation of the balloon 61, the blood vessel 80 is occluded on the distal side relative to the distal portion of the shaft main body 11. This can prevent the crushed thrombus from flowing in the blood vessel and moving to another place in the living body. Note that the balloon 61 may instead be a different type of occlusion member, such as a filter.

Figure 5:
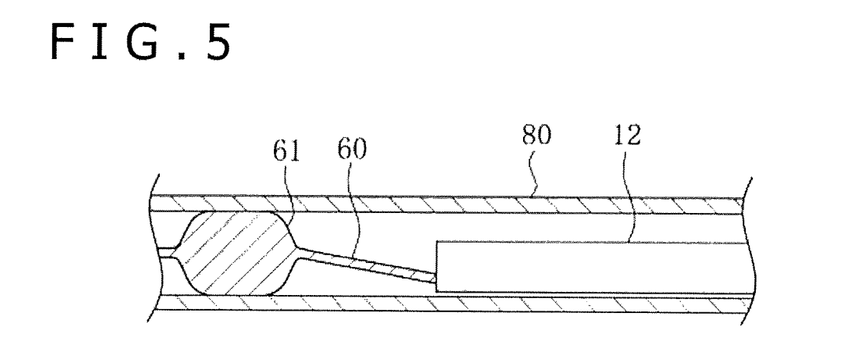
FIG. 5 is a sectional view of the state in which the shaft main body is inserted in a blood vessel and a balloon of a balloon catheter is inflated.

Next, the shaft main body 11 is inserted into the blood vessel 80. The shaft main body 11 is inserted while the shaft 60 of the balloon catheter is inserted in the rotation axis lumen 20. As shown in FIG. 5, the distal end of the outermost sheath body 12 in which the shaft main body 11 is housed is disposed at a position on the proximal side relative to the balloon 61. Note that the thrombus in the blood vessel 80 is omitted in the respective drawings. However, it is assumed that the thrombus is present near the distal end of the outermost sheath body 12 in FIG. 5.

Figure 6:
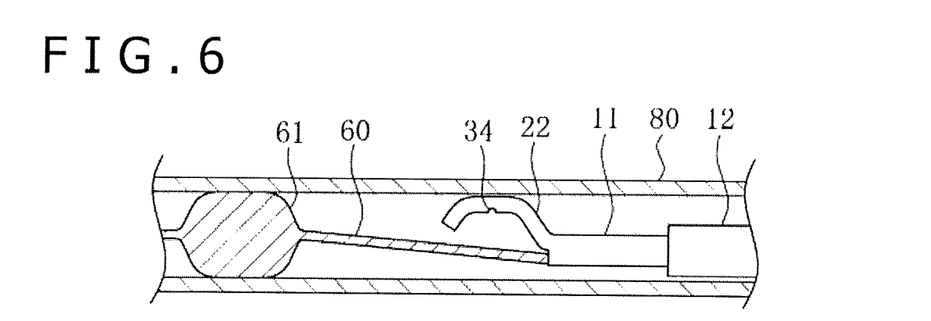
FIG. 6 is a sectional view of the state in which an outermost sheath body is made to retreat to expose the distal portion of the shaft main body.

Next, as shown in FIG. 6, the outermost sheath body 12 is slid to the proximal side to expose the distal portion of the shaft main body 11. Thereby, the distal shaft 22 of the shaft main body 11 housed in the outermost sheath body 12 is exposed and expands into the predetermined shape having the bending portion based on the proximal-side bending portion 31, the first distal-side bending portion 32, and the second distal-side bending portion 33.

Figure 7:
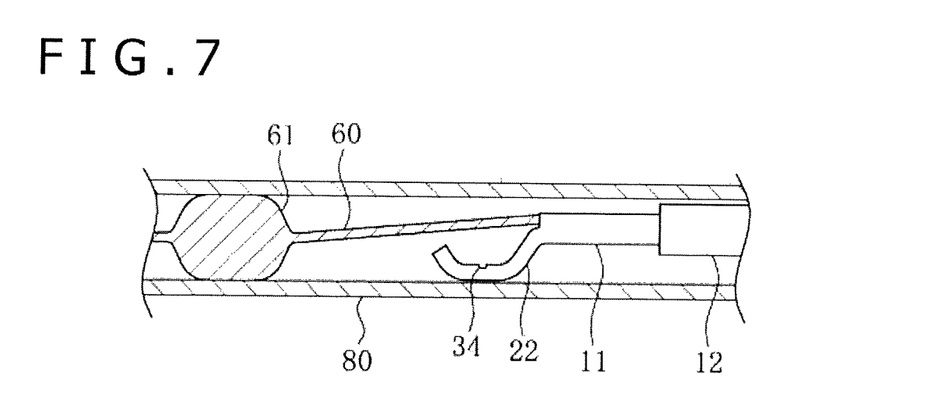
FIG. 7 is a sectional view of the state resulting from the rotation of the shaft main body by 180 degrees from the state of FIG. 6.

After the distal shaft 22 is exposed, the shaft main body 11 is rotationally moved around the rotation central axis of the rotation axis lumen 20 by the rotational drive unit 13. As shown in FIGS. 6 and 7, due to the rotation of the shaft main body 11 around the rotation central axis of the rotation axis lumen 20, the distal shaft 22, decentered from the rotation axis lumen 20, undergoes rotation with a relatively large radius of curvature in the sectional direction orthogonal to the axial direction of the blood vessel 80. Furthermore, the shaft main body 11 on the proximal side relative to the branch part 30 is also caused to swing or rotate in the blood vessel 80 because the rotation axis is present at a position decentered from the center. Moreover, in association with this, the shaft 60 of the balloon catheter inserted in the rotation axis lumen 20 is also caused to swing or rotate. Due to these movements, the thrombus in the blood vessel 80 is crushed and stirred. Due to the stirring of the crushed thrombus in the blood vessel 80, the crushed thrombus enters a state of being swirled up without sedimentation or the like in the blood vessel 80. That is, the shaft main body 11, the distal shaft 22, and the shaft 60 of the balloon catheter undergo respective rotations having three different maximum diameters.

Here, while the shaft main body 11 is rotated, the plunger of the syringe 15 is pulled back to set the inside of the revolving lumen 21 to a negative pressure state. Due to the setting of the inside of the revolving lumen 21 to the negative pressure state, the thrombus is sucked into the opening 34. Because the shaft main body 11 is rotating, the distal shaft 22, in which the opening 34 is made, is undergoing rotation with a relatively large radius of curvature in the sectional direction orthogonal to the axial direction of the blood vessel 80 as described above, and the thrombus can be effectively sucked over a wide range in the section in which the opening 34 is disposed. Furthermore, by reciprocating the shaft main body 11 in the axial direction of the blood vessel 80 in the suction of the thrombus, the thrombus can be sucked into the opening 34 in a wider range in the blood vessel 80.

After the suction of the thrombus, the rotation of the shaft main body 11 is stopped. Subsequently, the shaft main body 11 is housed in the outermost sheath body 12 and the balloon 61 is deflated. Then, the shaft main body 11 is pulled out from the blood vessel 80 together with the outermost sheath body 12.

Figure 8A:
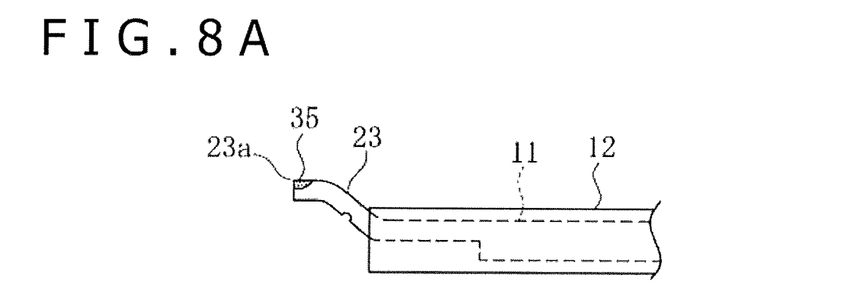
FIG. 8A is a front view of the state in which only the distal portion of a distal shaft of a first modification example is exposed from the outermost sheath body.
Figure 8B:
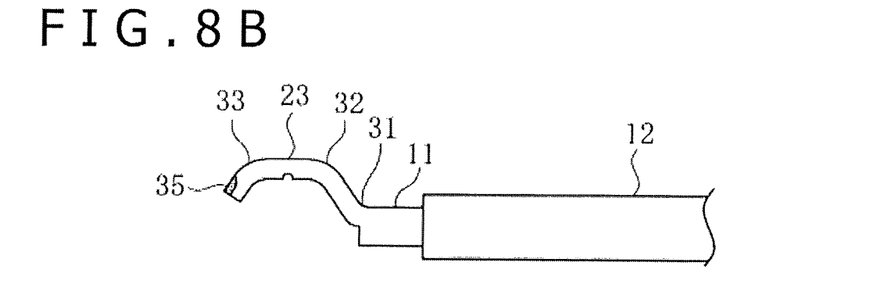
FIG. 8B is a front view of the state in which the whole of the distal shaft of the first modification example is exposed from the outermost sheath body.

Next, a first modification example of the distal shaft will be described. As shown in FIG. 8, a distal shaft 23 of the present modification example has a coarse surface portion 35 whose surface is coarser than the other portion at the outer circumferential part of the distal end.

FIG. 8A shows the state in which only the part around the distal portion of the distal shaft 23 is exposed from the outermost sheath body 12. At this time, the distal outer circumferential part of the distal shaft 23, in which the coarse surface portion 35 is formed, is in the state of being substantially parallel to the central axis of the rotation axis lumen 20 on the outer circumferential side relative to the outer circumferential surface of the outermost sheath body 12. When the shaft main body 11 is rotated around the rotation central axis of the rotation axis lumen 20 in this state, the coarse surface portion 35 is located at the outermost circumferential part in the rotation region formed by the shaft main body 11. Thus, the region in which the coarse surface portion 35 is formed is in the state of being oriented in the radial direction of the blood vessel 80.

FIG. 8B shows the state in which the whole of the distal shaft 23 is exposed from the outermost sheath body 12. At this time, the distal outer circumferential part of the distal shaft 23, in which the coarse surface portion 35 is formed, is in the state of being disposed closer to the rotation axis lumen 20, i.e., the inner circumferential side, than the region between the first distal-side bending portion 32 and the second distal-side bending portion 33 in the distal shaft 23. When the shaft main body 11 is rotated around the rotation central axis of the rotation axis lumen 20 in this state, the coarse surface portion 35 is located at a position on the inner circumferential side relative to the outermost circumferential part in the rotation region formed by the shaft main body 11. Thus, the region oriented in the radial direction of the blood vessel 80 is the region between the first distal-side bending portion 32 and the second distal-side bending portion 33.

As above, in the distal shaft 23, the position of the region oriented in the radial direction of the blood vessel 80 in the rotation differs depending on the state of the protrusion from the outermost sheath body 12. By forming the coarse surface portion 35 at any position as in the present embodiment, surfaces having different surface states can be selectively brought into contact with the thrombus or the like in the blood vessel 80. This can appropriately change the passage capability and following capability of the shaft main body 11 according to the state of the thrombus and so forth, enabling more flexible treatment. Note that a material having different hardness may be provided at part of the distal shaft 23 although the coarse surface portion 35 having a different surface state from the other portion is formed at the distal portion of the distal shaft 23 in the present embodiment. Furthermore, the region having the different surface state or hardness is not limited to the distal portion and may be another region.

Furthermore, the length of the distal shaft 23 in the radial direction of the blood vessel 80 can be changed depending on the state of the protrusion from the outermost sheath body 12. Therefore, the diameter at the time of rotation can be changed in the sectional direction orthogonal to the axial direction of the blood vessel 80. The maximum diameter is obtained when the proximal-side bending portion 31 of the distal shaft 23 protrudes from the distal end of the outermost sheath body 12. The minimum diameter is obtained when a most distal end 23a of the distal shaft 23 protrudes from the distal end of the outermost sheath body 12. Furthermore, it is also possible to rotate the shaft main body 11 in the state in which the first distal-side bending portion 32 and the second distal-side bending portion 33 protrude from the distal end of the outermost sheath body 12.

Figure 9:
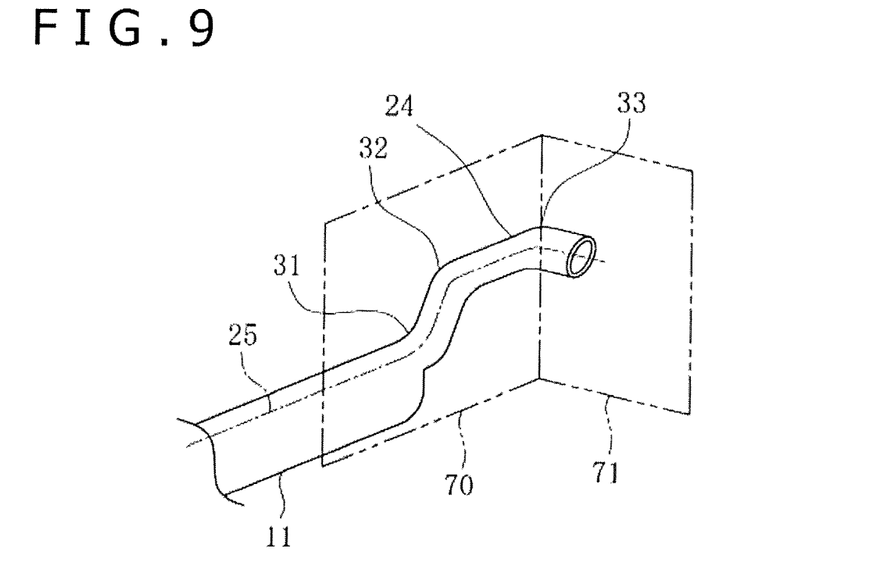
FIG. 9 is a perspective view of a part around a distal shaft of a second modification example.

Next, a second modification example of the distal shaft will be described. As shown in FIG. 9, a distal shaft 24 of the present modification example is the same as the distal shafts described thus far with respect to the proximal-side bending portion 31 and the first distal-side bending portion 32. In the region from the branch part 30 to the second distal-side bending portion 33, the central axis of a revolving lumen 25 is located in a first plane 70. On the other hand, with respect to the region on the distal side relative to the second distal-side bending portion 33, the central axis of the revolving lumen 25 is located in a second plane 71 intersecting the first plane 70.

The distal shafts described thus far both have a two-dimensional shape in which the central axis of the revolving lumen 21 is located in the same plane. However, in the distal shaft 24 of the present modification example, the central axis of the revolving lumen 25 bends to extend across the two planes intersecting each other. Thus, the distal shaft 24 has a three-dimensional shape.

In insertion of the shaft main body 11, the rotation axis lumen 20 is guided by a guide wire. However, the distal shaft 24 branches from the side of the rotation axis lumen 20 and the guide wire is not inserted therein. Thus, there is a possibility that the distal shaft 24 may enter a different blood vessel from the side of the rotation axis lumen 20 at a branch part of a blood vessel. In the present modification example, with the three-dimensional shape, the distal shaft 24 is inserted while coming into contact with plural positions that are different in the axial direction and the circumferential direction on the blood vessel inner wall. This allows the distal shaft 24 to readily follow the motion of the rotation axis lumen 20, which can prevent entry of the distal shaft 24 into another blood vessel.

When the shaft main body 11 is inserted into a blood vessel having a small inner diameter, it is necessary to leave a space in which the distal portion of the shaft main body 11 can slide. If the distal shaft has a two-dimensional shape, the bending direction of the distal shaft is limited and therefore it is necessary to leave a space equivalent to the diameter of the distal shaft. By contrast, in the case of the distal shaft 24 having the three-dimensional shape, the flexibility in the shape housed in a blood vessel becomes higher. Thus, sliding can occur in a smaller space, resulting in a widening of the range of the blood vessel diameter which can be treated by the catheter system 10.

In FIG. 9, the distal shaft in which the second distal-side bending portion 33 bends in one direction is shown. However, a larger number of bending portions may be provided and it is also possible to form the bending portions in such a manner that the respective bending portions bend toward different plane sides. Furthermore, the shaft main body 11 in which the distal portion of the distal shaft has a helical shape along the axial direction is also included. If the distal shaft has a helical shape, the slidability of the distal shaft in the blood vessel can be made more favorable.

Figure 10:
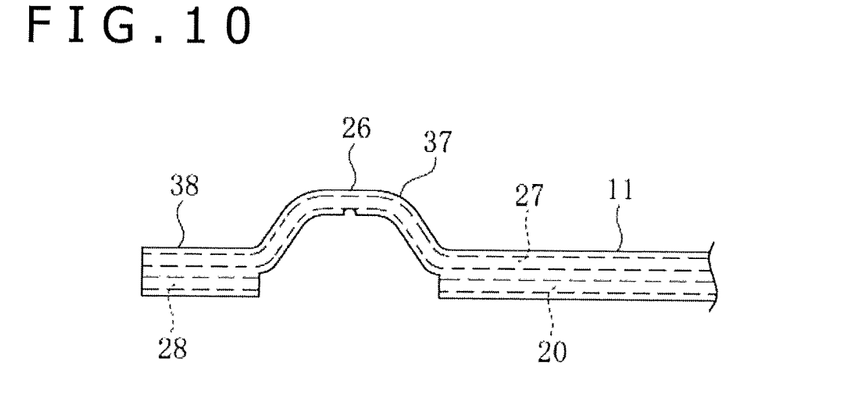
FIG. 10 is a front view of a part around a distal shaft of a third modification example.

Next, a third modification example of the distal shaft will be described. As shown in FIG. 10, in a distal shaft 26 of the present modification example, a single-lumen portion 37 having only a revolving lumen 27 extends from the branch part 30 toward the distal side. Furthermore, at the distal end of the single-lumen portion 37, the distal shaft 26 has a double-lumen portion 38 in which two lumens, the revolving lumen 27 and a distal lumen 28, are juxtaposed. The distal lumen 28 has an inner diameter equivalent to that of the rotation axis lumen 20 and the guide wire and the shaft 60 of the balloon catheter can be inserted therein. The opening 34 is made in the single-lumen portion 37.

By forming the double-lumen portion 38 having the revolving lumen 27 and the distal lumen 28 at the distal portion of the distal shaft 26 in this manner, the entry of the distal shaft 26 from a branch part of a blood vessel into a different blood vessel from the side of the rotation axis lumen 20 can be prevented when the guide wire is inserted also into the distal lumen 28 and the shaft main body 11 is inserted into the blood vessel. Furthermore, the distal shaft 26 is also guided into the blood vessel by the guide wire and thus smoother insertion operation can be carried out.

Figure 11A:
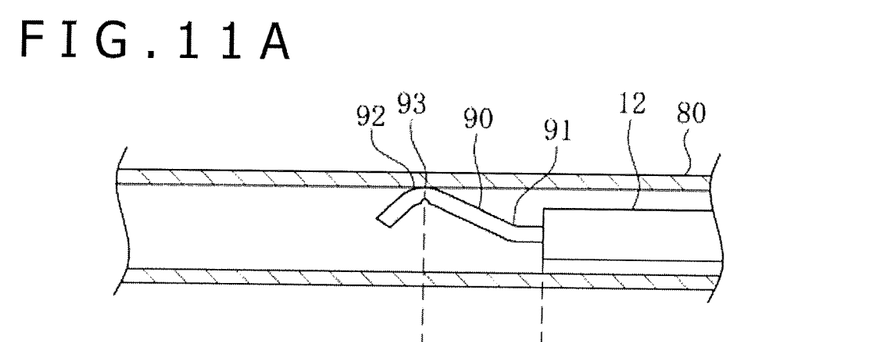
Figure 11B:
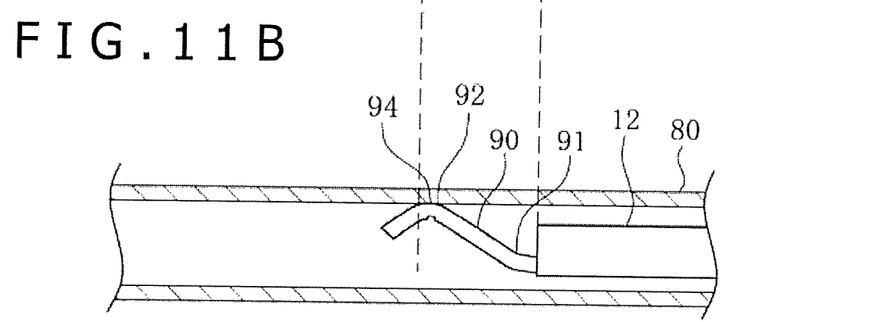

Next, a fourth modification example of the distal shaft will be described. As shown in FIG. 11A, a distal shaft 90 of the present modification example has a proximal-side bending portion 91 and a distal-side bending portion 92 at the part protruding from the outermost sheath body 12 toward the distal side. As shown in FIG. 11A, in the state in which the distal shaft 90 is present at the central position of the outermost sheath body 12 in the radial direction, the distal shaft 90 is in contact with the blood vessel 80 at the position of a contact part 93. On the other hand, as shown in FIG. 11B, in the state in which the distal shaft 90 moves in the radial direction of the outermost sheath body 12 and is located at the peripheral part of the outermost sheath body 12, the position of a contact part 94 at which the distal shaft 90 is in contact with the blood vessel 80 changes. Here, the distal shaft 90 moves toward the lower side in the diagram. Due to this, the position of the contact part 94 in this state moves toward the proximal side relative to the contact part 93 in the state in which the distal shaft 90 is present at the central position of the outermost sheath body 12 in the radial direction. By changing the position of the contact of the distal shaft 90 with the blood vessel 80 in association with changing the position of the distal shaft 90 in the radial direction of the outermost sheath body 12 in this manner, the thrombus can be crushed and sucked along with the rotation of the shaft main body 11 over a wider range in the blood vessel 80.

Figure 12:
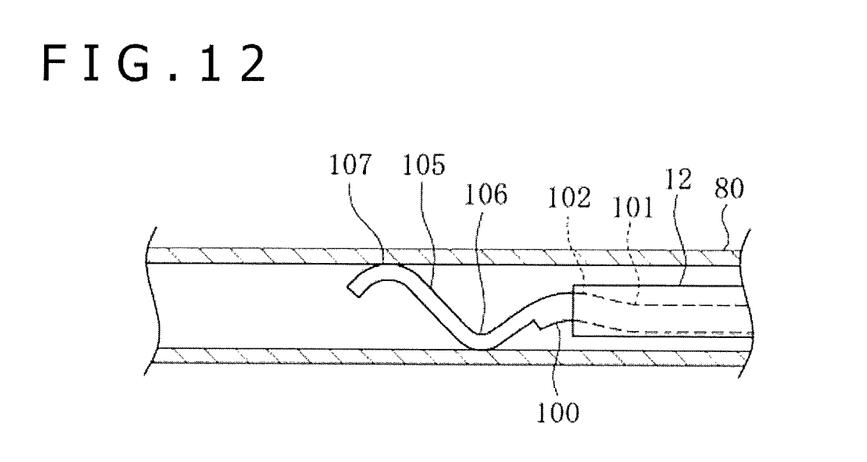
FIG. 12 is a front view of a part around a distal shaft of a fifth modification example.

Next, a fifth modification example of the distal shaft will be described. In the present modification example, a bending portion is also provided in a shaft main body 100. As shown in FIG. 12, near the distal end of the shaft main body 100, a proximal-side bending portion 101 that bends in one direction and a distal-side bending portion 102 that bends toward the opposite side to the proximal-side bending portion 101 are formed. Furthermore, in a distal shaft 105, a proximal-side bending portion 106 that bends toward the opposite side to the distal-side bending portion 102 of the shaft main body 100 and a distal-side bending portion 107 that bends toward the opposite side to this proximal-side bending portion 106 are formed. Due to these bending portions, the shaft main body 100 and the distal shaft 105 exposed from the outermost sheath body 12 have an S-shape in the blood vessel 80. Furthermore, the distal shaft 105 contacts with the inner wall of the blood vessel 80 on one side at the proximal-side bending portion 106 of the distal shaft 105, and contacts with the inner wall of the blood vessel 80 on the opposite side at the distal-side bending portion 107 of the distal shaft 105. The shaft main body 100 and the distal shaft 105 having such a shape are rotated around the rotation central axis of the rotation axis lumen 20. Thereby, the distal shaft 105 undergoes rotation with a relatively large radius of curvature in the section orthogonal to the axial direction in the blood vessel 80 and the thrombus in a wider range can be crushed and sucked. Note that a larger number of bending portions may be provided as the bending portions of the shaft main body 100 and the distal shaft 105.

Figure 13:
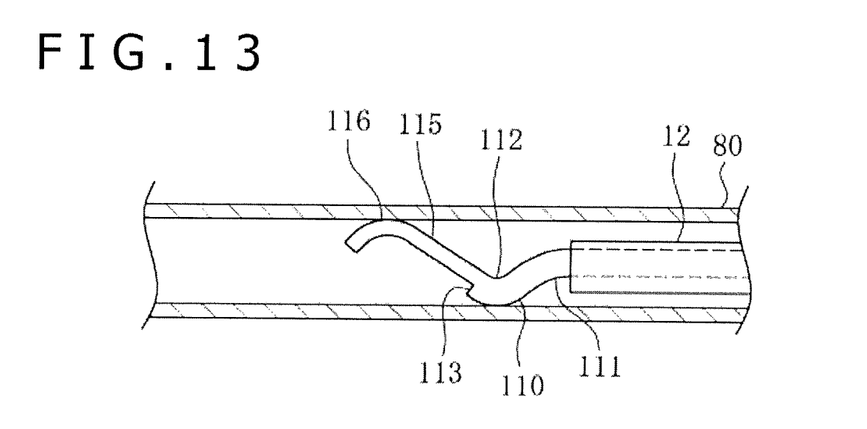
FIG. 13 is a front view of a part around a distal shaft of a sixth modification example.

Next, a sixth modification example of the distal shaft will be described. In the present modification example, bending portions are formed in a shaft main body 110 similarly to the fifth modification example. As shown in FIG. 13, in the shaft main body 110, a proximal-side bending portion 111 and a distal-side bending portion 112 that bends toward the opposite side to the proximal-side bending portion 111 are formed. Among these, the distal-side bending portion 112 is exposed from the outermost sheath body 12 to the distal side and contacts with the inner wall of the blood vessel 80 on one side. A distal shaft 115 has a bending portion 116 and contacts with the inner wall of the blood vessel 80 on the opposite side. By forming the shaft main body 110 and the distal shaft 115 in this manner, the same effects as in the fifth modification example can be achieved. In addition, an opening 113 of the rotation axis lumen is disposed between the distal-side bending portion 112 of the shaft main body 110 and the bending portion 116 of the distal shaft 115. This can allow the shaft 60 of the balloon catheter inserted into the rotation axis lumen to be readily oriented in a straight direction along the axial direction in the blood vessel 80, which can make the movement of the shaft main body 110 smooth. Furthermore, in the state in which the distal shaft 115 is present at the central position of the outermost sheath body 12 in the radial direction, the distal shaft 115 is in contact with the blood vessel 80 at the position of numeral 116. On the other hand, in the state in which the distal shaft 115 has moved in the radial direction of the outermost sheath body 12 and is located at the peripheral part of the outermost sheath body 12, the position of the contact part at which the distal shaft 115 is in contact with the blood vessel 80 changes and simultaneously the position of the contact of the shaft main body 110 with the blood vessel 80 also changes.

As described above, the catheter system 10 according to the present embodiment has a shaft main body 11 with an elongated shape. The shaft main body 11 has the rotation axis lumen 20 including the rotation central axis and the revolving lumen 21 that revolves around the rotation axis lumen 20. Furthermore, the distal side relative to the branch part 30 branches in the rotation axis lumen 20 and the revolving lumen 21, and the revolving lumen 21 on the distal side relative to the branch part 30 is formed of the distal shaft 22. Moreover, the distal shaft 22 has the proximal-side bending portion 31 that bends in such a direction as to become farther away from the rotation axis lumen 20 in the radial direction and the opening 34 that communicates with the revolving lumen 21. Thus, in association with the rotation of the rotation axis lumen 20, the revolving lumen 21 revolves around the rotation axis lumen 20 and the distal shaft 22 having the bending portion 31 undergoes rotation with a relatively large radius of curvature in the section orthogonal to the axial direction of the blood vessel 80. This configuration can easily suck the thrombus thoroughly over a wide range in the blood vessel 80.

Furthermore, if the protective shaft 60 that protrudes to the distal side relative to the distal shaft 22 is inserted into the rotation axis lumen 20 and the protective member 61 that limits the flow of a fluid in a living body lumen is provided on the distal side of the protective shaft 60, a thrombus portion broken off during suction of the thrombus can be inhibited from flowing in a blood vessel 80 and moving to another place.

In addition, if the distal shaft 22 has one or plural distal-side bending portions 32 and 33 that bend in a different direction from the proximal-side bending portion 31, the effect of stirring the inside of the living body lumen by the distal shaft 22 when the shaft main body 11 rotates can be made large and the thrombus can be made to float in the living body lumen and efficiently sucked.

Moreover, if the central point that defines the radius of curvature of the central axis is located closer to the central axis of the rotation axis lumen 20 than the distal shaft 22 regarding at least one of the distal-side bending portions 32 and 33, the distal surface of the distal shaft can be prevented from being oriented toward the inner wall surface of the living body lumen, and damage given to the living body lumen by the distal shaft 22 when the shaft main body is rotated can be reduced.

Furthermore, if the central axis of the revolving lumen 25 from the branch part 30 to any one distal-side bending portion 33 is located in the first plane 70 and at least part of the central axis of the revolving lumen 25 on the distal side relative to this distal-side bending portion 33 is located in the second plane 71 intersecting the first plane 70, the distal shaft 24 comes into contact with plural places different in the axial direction and the circumferential direction on the inner wall of the living body lumen when the shaft main body 11 is inserted. This configuration can make the following capability with respect to the side of the rotation axis lumen 20 favorable. Furthermore, because the distal shaft 24 has a three-dimensional shape, when the distal shaft is inserted into a living body lumen having a small diameter, the flexibility in deformation is high and the slidability can be made favorable.

In addition, if the opening 34 is disposed to face the inside in the radial direction of rotation across the whole circumference when the distal shaft 22 rotates around the rotation central axis of the rotation axis lumen 20, the opening 34 can be prevented from being oriented toward the inner wall side of the living body lumen when the shaft main body 11 is rotated, so that damage given to the living body lumen can be reduced.

Moreover, if a balloon catheter having the balloon 61 at the distal portion of the shaft 60 is inserted into the rotation axis lumen 20 and the shaft 60 of the balloon catheter inserted to the distal side relative to the distal shaft 22 is caused to swing or rotate when the shaft main body 11 rotates around the rotation central axis of the rotation axis lumen 20, not only the shaft main body 11 but also the shaft 60 of the balloon catheter swings or rotates in the living body lumen and thus the thrombus can be crushed and stirred more effectively.

Furthermore, if the shaft main body 11, the distal shaft 22, and the shaft 60 of the balloon catheter each rotate at a different maximum diameter when the shaft main body 11 rotates around the rotation central axis of the rotation axis lumen 20, the shaft main body 11, the distal shaft 22, and the shaft 60 of the balloon catheter rotate in a wide range in the living body lumen and thus the crushing and stirring of the thrombus can be made more effective.

In addition, the present disclosure also provides a treatment method for removing an object generated at a lesion site in a living body lumen by suction. This treatment method is carried out by using the following catheter. Specifically, the catheter has a shaft main body having an elongated shape. The shaft main body has a rotation axis lumen including the rotation central axis and a revolving lumen that revolves around the rotation axis lumen. Furthermore, the distal side relative to a branch part branches in the rotation axis lumen and the revolving lumen, and the revolving lumen on the distal side relative to the branch part is formed of a distal shaft. Moreover, the distal shaft has a proximal-side bending portion that bends in such a direction as to become farther away from the rotation axis lumen in the radial direction and an opening that communicates with the revolving lumen. This treatment method includes (i) inserting the shaft main body into a living body lumen and delivering a distal portion to a lesion site, (ii) rotating the shaft main body around the rotation central axis of the rotation axis lumen, (iii) performing suction of the revolving lumen to make a negative pressure state, (iv) sucking a thrombus into the opening, and (v) stopping the suction of the revolving lumen and the rotation of the shaft main body and pulling out the shaft main body from the inside of the living body lumen. According to this treatment method, in association with the rotation of the rotation axis lumen, the revolving lumen revolves around the rotation axis lumen and the distal shaft having the bending portion undergoes rotation with a relatively large radius of curvature in the section orthogonal to the axial direction of a blood vessel. This configuration can easily suck the thrombus thoroughly over a wide range in the blood vessel.

In the above-described treatment method, a protective shaft having a protective member that limits the flow of a fluid in the living body lumen may be inserted into the living body lumen before the shaft main body is inserted into the living body lumen. This configuration can inhibit a thrombus portion broken off during the suction of the thrombus from flowing in the blood vessel and moving to another place.

Furthermore, in the above-described treatment method, an outermost sheath body that houses the shaft main body may be further provided, and the outermost sheath body may be slid to expose the distal shaft after the distal portion of the shaft main body is delivered to the lesion site. Due to this, the part oriented in the radial direction in the distal shaft differs depending on the length of the exposed part in the distal shaft from the outermost sheath body. By providing a region whose surface state or material is different at one part of the distal shaft, different states of contact with the living body lumen can be selectively used according to the length of the protrusion of the distal shaft from the outermost sheath body.

Moreover, in the above-described treatment method, the shaft main body may be reciprocated in the axial direction of the living body lumen while sucking a thrombus into the opening. In addition, the shaft main body may be reversely rotated. This configuration can suck the thrombus in a wider region in the living body lumen.

Note that the present disclosure is not limited to only the above-described embodiment and various changes can be made by those skilled in the art in the technical thought of the present disclosure. For example, although the shaft main body 11 is rotationally driven by the rotational drive unit 13 having the drive motor 40 in the present embodiment, the drive source is not limited and may be, e.g., a gas turbine that rotates by a high-pressure gas such as a nitrogen gas.

Furthermore, in the above-described embodiment, the opening 34 is present at an intermediate position of the distal shaft 22 in the axial direction and the revolving lumen 21 is occluded at the distal end of the distal shaft 22. However, the distal end of the distal shaft 22 may be formed into an open shape and this distal end may be used as the opening.

The detailed description above describes a catheter system. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A catheter system comprising:
a shaft main body having an elongated shape, a rotation axis lumen including a rotation central axis, and a revolving lumen that revolves around the rotation axis lumen when the shaft main body is rotated about the rotation central axis,
a protective shaft that is inserted into the rotation axis lumen and protrudes from the rotation axis lumen; and
a protective member provided on a distal side of the protective shaft and configured to limit flow of a fluid in a living body lumen; wherein the shaft main body includes a side-by-side portion in which at least a portion of the rotation axis lumen and a portion of the revolving lumen exist in side-by-side relationship;

the shaft main body includes a branch part at which the revolving lumen branches off from the side-by-side portion to form a distal shaft that is not in side-by-side relationship with the rotation axis lumen, the protective shaft protruding further distally than the distal shaft, and the distal shaft has a proximal-side bending portion that bends in such a direction as to become farther away from the rotation axis lumen in a radial direction and an opening that communicates with the revolving lumen.

2. The catheter system according to claim 1, wherein the distal shaft has one or a plurality of distal-side bending portions that bend in a different direction from the proximal-side bending portion.

3. The catheter system according to claim 2, wherein for at least one of the distal-side bending portions, a central point that defines a radius of curvature of a central axis of the revolving lumen at the distal-side bending portion is located between the rotation central axis and the distal-side bending portion.

4. The catheter system according to claim 2, wherein a central axis of the revolving lumen from the branch part to any one of the distal-side bending portions is located in a first plane and at least part of the central axis of the revolving lumen on the distal side relative to the distal-side bending portion is located in a second plane intersecting the first plane.

5. The catheter system according to claim 1, wherein the opening is disposed to face inside in the radial direction of rotation across a whole circumference when the distal shaft rotates around the rotation central axis of the rotation axis lumen.

6. The catheter system according to claim 1, wherein:
the protective member comprises a balloon catheter having a balloon, and
the protective shaft is caused to swing or rotate when the shaft main body rotates around the rotation central axis of the rotation axis lumen.

7. The catheter system according to claim 6, wherein the side-by-side portion, the distal shaft, and the protective shaft each rotate at a different maximum diameter when the shaft main body rotates around the rotation central axis of the rotation axis lumen.

8. A catheter system comprising:
a shaft main body having an elongated shape and a lumen defining an axis of the shaft main body, said lumen being in communication with an opening;
a distal shaft for aspiration having a distal end on a distal side of the opening and being disposed such that a distance between the distal shaft and the axis increases toward the distal end of the distal shaft;
a suction apparatus in communication with a lumen of the distal shaft; and
a balloon catheter or a filter positionable in the lumen of the shaft main body during aspiration.

9. The catheter system according to claim 8, wherein a distalmost end portion of the shaft main body is parallel to the axis of the shaft main body.

10. The catheter system according to claim 8, wherein the suction apparatus comprises a syringe.

11. A catheter system comprising:
a shaft main body having an elongated shape and a lumen defining an axis of the shaft main body, said lumen being in communication with an opening;
a distal shaft for aspiration having a distal end on a distal side of the opening and being disposed such that a distance between the distal shaft and the axis increases toward the distal end of the distal shaft;
a balloon catheter or a filter positionable in the lumen of the shaft main body during aspiration; and
a suction apparatus in communication with a lumen of the distal shaft and with the lumen of the main shaft body.

12. The catheter system according to claim 11, wherein the suction apparatus comprises a syringe.

* * * * *